(12) United States Patent
Minassians

(10) Patent No.: US 8,246,552 B2
(45) Date of Patent: Aug. 21, 2012

(54) CLOSED SPECIMEN COLLECTION SYSTEM

(76) Inventor: Nastaran Minassians, La Crescenta, CA (US)

( * ) Notice: Subject to any disclaimer, the term of this patent is extended or adjusted under 35 U.S.C. 154(b) by 942 days.

(21) Appl. No.: 12/209,025

(22) Filed: Sep. 11, 2008

(65) Prior Publication Data

US 2009/0076414 A1   Mar. 19, 2009

Related U.S. Application Data

(63) Continuation-in-part of application No. 11/858,073, filed on Sep. 19, 2007, now Pat. No. 7,875,021.

(51) Int. Cl.
*A61B 5/00* (2006.01)
*B65D 81/00* (2006.01)

(52) U.S. Cl. ........ 600/573; 600/576; 600/577; 600/580; 600/582; 604/48; 604/508; 604/541

(58) Field of Classification Search .......... 600/573–583; 604/517, 523, 533, 544, 48, 508, 541; 128/207.14, 128/207.16
See application file for complete search history.

(56) References Cited

U.S. PATENT DOCUMENTS

| | | | |
|---|---|---|---|
| 2,871,857 A * | 2/1959 | Lipari | 604/236 |
| 2,992,974 A * | 7/1961 | Belcove et al. | 435/288.1 |
| 3,579,303 A | 5/1971 | Pickering | |
| 4,062,363 A | 12/1977 | Bonner, Jr. | |
| 4,068,659 A | 1/1978 | Moorehead | |
| 4,136,680 A * | 1/1979 | Southworth | 600/572 |
| 4,190,059 A | 2/1980 | Holt | |
| 4,327,723 A | 5/1982 | Frankhouser | |
| 4,515,592 A | 5/1985 | Frankhouser | |
| 4,702,740 A | 10/1987 | Bates | |
| 4,753,638 A | 6/1988 | Peters | |
| 4,932,938 A | 6/1990 | Goldberg et al. | |
| 4,966,585 A * | 10/1990 | Gangemi | 604/131 |
| 4,972,844 A | 11/1990 | Cianci et al. | |
| 4,981,469 A * | 1/1991 | Whitehouse et al. | 604/86 |
| 5,096,454 A | 3/1992 | Samples | |
| 5,108,927 A | 4/1992 | Dorn | |
| 5,114,400 A * | 5/1992 | Lynn | 604/540 |
| 5,140,999 A | 8/1992 | Ardito | |
| 5,176,655 A * | 1/1993 | McCormick et al. | 604/198 |
| 5,176,665 A | 1/1993 | Watanabe et al. | |
| 5,365,960 A | 11/1994 | Bran | |
| 5,409,459 A | 4/1995 | Gambale | |
| 5,501,669 A | 3/1996 | Conway et al. | |
| 5,511,557 A | 4/1996 | Hazard et al. | |
| 5,531,255 A * | 7/1996 | Vacca | 141/285 |
| 5,595,187 A * | 1/1997 | Davis | 600/584 |
| 5,637,091 A | 6/1997 | Hakky et al. | |

(Continued)

*Primary Examiner* — Rene Towa

(74) *Attorney, Agent, or Firm* — David A. Belasco; Belasco Jacobs & Townsley, LLP

(57) ABSTRACT

A closed specimen collection system for blood samples includes a collection tube that has a shaped nozzle adapted to fit sealably into a port connected to a centrally inserted venal catheter. A protective cover for the nozzle is attached to the collection tube and has an internal, female thread that mates to a male thread on the port. A specimen container has a hollow body, a front end and a back end. The front end has an aperture sized and shaped to attach to the collection tube. The aperture is sealable after removal of the collection tube. A piston fits closely within the hollow body and is attached to an actuating rod. When the port is connected to the collection tube, the collection tube is connected to the specimen container and the actuating rod is pulled toward the back end, blood will flow into the container in a sterile condition.

10 Claims, 6 Drawing Sheets

U.S. PATENT DOCUMENTS

| | | |
|---|---|---|
| 5,785,694 A | 7/1998 | Cohen et al. |
| 5,979,475 A | 11/1999 | Satoh et al. |
| 5,993,436 A | 11/1999 | Kitou et al. |
| 6,045,542 A | 4/2000 | Cawood |
| 6,235,010 B1 | 5/2001 | Wilkinson et al. |
| 6,315,145 B1* | 11/2001 | Fask et al. .................. 220/254.1 |
| 6,440,119 B1 | 8/2002 | Nakada et al. |
| 6,511,459 B1* | 1/2003 | Fago ............................ 604/181 |
| 6,732,875 B2 | 5/2004 | Smith et al. |
| 6,743,198 B1 | 6/2004 | Tihon |
| 6,783,522 B2 | 8/2004 | Fischell |
| 6,793,651 B1 | 9/2004 | Bennett et al. |
| 6,827,705 B2 | 12/2004 | Bierman |
| 6,830,563 B1 | 12/2004 | Singer |
| 6,913,244 B1 | 7/2005 | Atkinson et al. |
| 7,150,740 B2 | 12/2006 | Bennett et al. |
| 2005/0031493 A1* | 2/2005 | Kipke et al. .................... 422/99 |
| 2006/0185448 A1* | 8/2006 | Sakal et al. .................... 73/863 |

\* cited by examiner

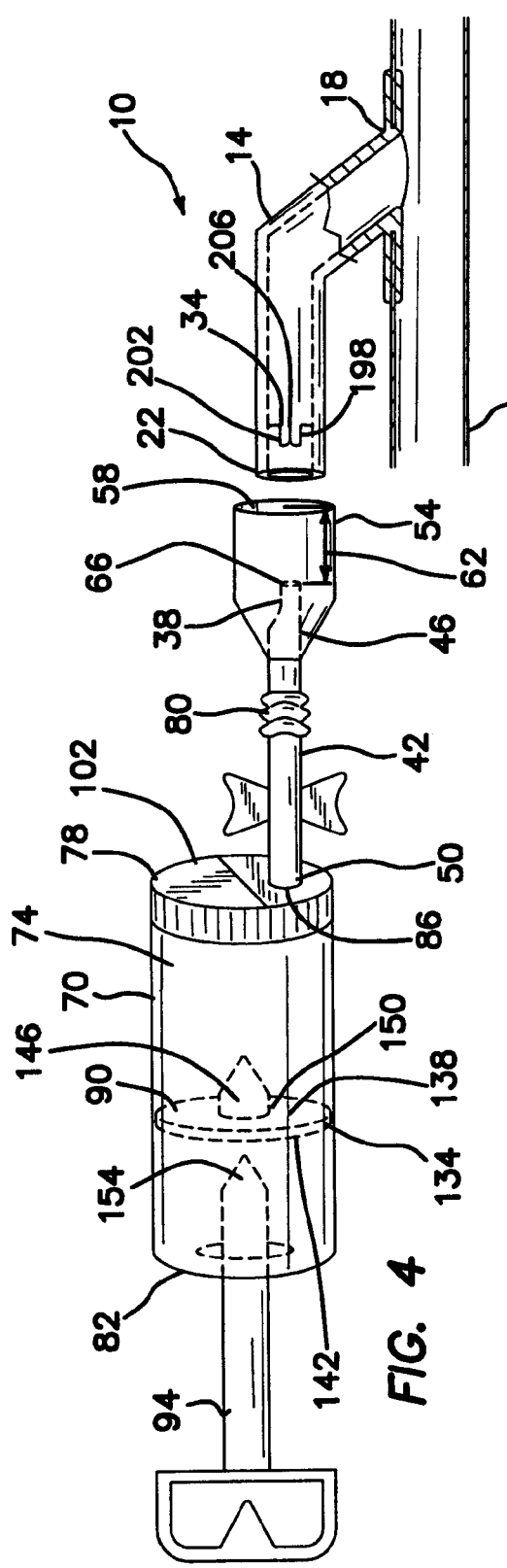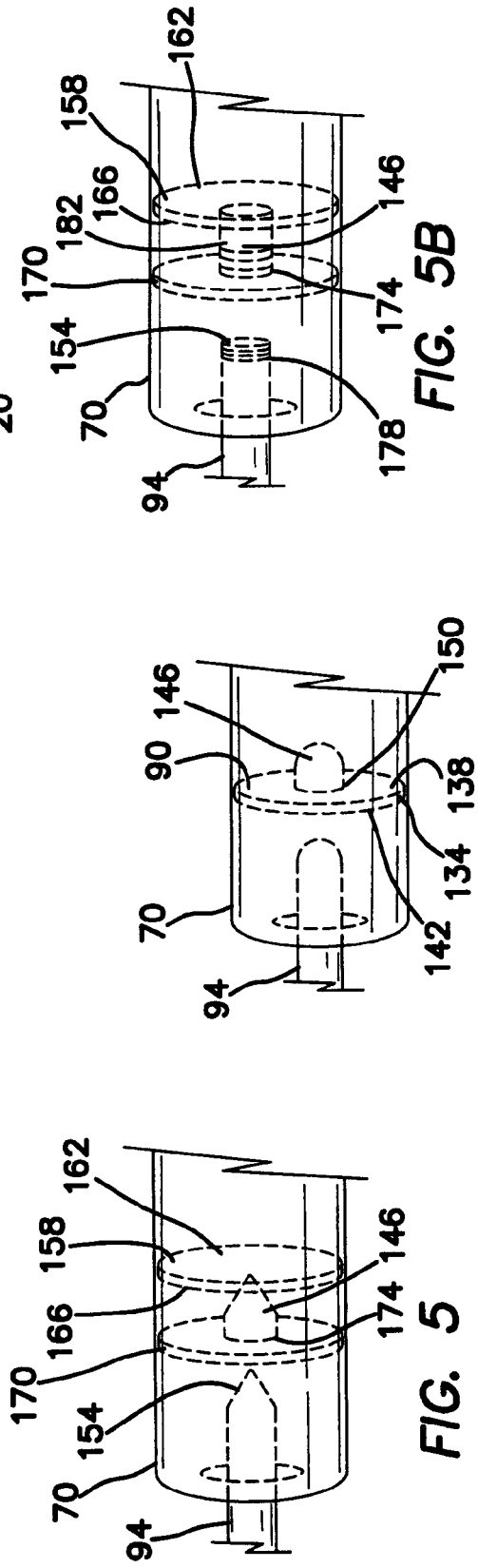

CLOSED SPECIMEN COLLECTION SYSTEM

RELATED APPLICATION

This application is a continuation-in-part of U.S. application Ser. No. 11/858,073, filed Sep. 19, 2007 now U.S. Pat. No. 7,875,021 and incorporates the same as if written herein.

FIELD OF INVENTION

This invention relates to the field of fluid specimen collection, and more specifically to a system for obtaining sterile blood specimens without the use of aspirating needles.

BACKGROUND OF THE INVENTION

Health care providers are frequently required to obtain blood specimens from patients for laboratory testing. In hospital environments, patients are often catheterized when their conditions require them to be bedridden. While present systems allow for nurses and other health care workers to obtain blood specimens from the patient's centrally inserted venal catheter, such systems require the use of syringes and are difficult and potentially dangerous, both to the health care provider and to the patient. The dangers arise from the use of syringes, which can result in accidental needle sticks, and from infections introduced through non-sterile interfaces for obtaining the specimens. The present systems use a rubber membrane on a fixed port of tubing attached to the catheter. This membrane is penetrated with a syringe which is used to withdraw the specimen. The rubber membrane may become contaminated and thereby compromise the specimen or infect the patient. The present invention seeks to eliminate these problems and provide a system that is both safer an easier to use.

U.S. Pat. No. 6,793,651, issued to Bennett et al., discloses a urinary catheter system that includes a urinary catheter, a connector and a medical implement which is readily attached to or removed from the connector. When a medical implement such as a collection appliance is attached to the connector, fluid such as urine can flow from the patent and into the collection appliance. Alternatively, when a syringe is attached to the connector, the catheter system may be irrigated to remove debris and other foreign matter, or the syringe may be used to provide medication to the patient. The system is preferably a closed system in which the connector includes a resealable valve which prevents the flow of fluid through the connector if a medical implement is not attached.

U.S. Pat. No. 6,045,542, issued to Cawood is directed to a flat urinary drainage bag that can be worn by a patient over the abdomen with the bag suspended from a waist-encircling belt is disclosed. The device includes an inlet tube for connection to a urethral catheter and a valve-equipped drain tube that extends downwardly from the bag when the drain tube is used to drain the contents there from. The lower end of the bag is foldable upwardly to position the drain tube in an upwardly-facing raised position against the bag's front wall, and a retaining strap is located across the front wall for holding the drain tube in its raised position. Spot attachments that secure the ends of the strap to the bag's front wall also secure the front and rear walls of the bag together, thereby performing multiple functions of limiting bulging of the bag in use, reducing sloshing of the bag's contents, and securing the retaining strap (and the raised drainage tube) in place.

U.S. Pat. No. 5,176,665, issued to Watanabe et al. discloses an antimicrobial device adapted for passage through the drainage port of a urinary drainage container. This invention concerns also a patient-care system comprising, in combination, a urinary drainage container comprising a drainage port for inserting an antimicrobial device into the container, and an antimicrobial delivery device. The antimicrobial device delivers an agent into the container for preventing and eliminating unwanted pathogens inside the container. The invention relates also to a method for preventing and eliminating unwanted pathogens in a urine receiving container by inserting through the drainage exit into the container, a device for delivering an antimicrobial agent in the container.

U.S. Pat. No. 4,723,950, issued to Lee discloses a urine drainage bag having an outlet tube housing a microcidal tube is disclosed. The microcidal tube is manufactured from polymeric materials capable of absorbing and releasing antimicrobial substances in a controllable sustained time release mechanism, activated upon contact with droplets of urine, thereby preventing the retrograde migration of infectious organisms into the drainage bag.

U.S. Pat. No. 4,784,654, issued to Beecher is directed to an improved female urinary appliance is disclosed. The appliance includes a mouth surrounding a urine-receiving cavity, and a drainage channel. The mouth is adapted to be positioned within the labia folds of the user, in contact with the vestibular tissue around the meatus and held in place by gentle vacuum. A valve is preferably used in combination with the appliance, and includes an inlet and an outlet, for maintaining a preselected vacuum condition at the valve inlet and a predetermined pressure condition at the valve outlet is disclosed. In preferred use, the drainage channel is suitable connected in spaced relation to the valve inlet. The valve contains a flow control element adapted to control flow of urine from the cavity. While the mouth is held against the vestibular tissue by gentle vacuum, urine flowing through the appliance and valve entrains gas present in the cavity. In the cavity, a desired vacuum condition is maintained, over time, because the valve includes a semi-permeable membrane adapted to permit air and other gas to diffuse through a portion of the valve and thereby to counteract the effects of entrainment and relieve or maintain the vacuum condition at a predetermined level.

U.S. Pat. No. 4,702,740, issued to Bates discloses a collection system for body fluids comprising, a receptacle having a collection chamber for retaining the body fluids, a first container having a supply chamber for retaining a bactericide, and a second container having a holding chamber, with the holding chamber being located above a lower portion of the collection chamber, and the supply chamber being located above a lower portion of the holding chamber. The system has a first valve member permitting the passage of bactericide from the supply chamber into the holding chamber, and a second valve member permitting the passage of the bactericide from the holding chamber into the collection chamber.

It is an objective of the present invention to provide a system for collection of blood from patients with centrally inserted venal catheters that will prevent the contamination of the blood so that it can be used for laboratory procedures. It is a further objective to provide such a system that will prevent infection of the patient due to procedures used for obtaining the samples. It is a still further objective of the invention to provide the above features without the use of syringes. It is yet a further objective to provide a system that can be used for introducing medication to a patient's blood supply. It is yet another objective to provide a system that can be used for easily culturing blood samples without transferring the sampled blood to another container. Finally, it is an objective of the present invention to provide such a system that is reliable, inexpensive to produce and disposable.

While some of the objectives of the present invention are disclosed in the prior art, none of the inventions found include all of the requirements identified.

SUMMARY OF THE INVENTION

The present invention addresses all of the deficiencies of prior art closed specimen collection system inventions and satisfies all of the objectives described above.

(1) A closed specimen collection system for urine samples providing the desired features may be constructed from the following components. A port tube is provided. The port tube has a first end, a second end and is rotatably attached at the first end to tubing of a urinary drainage system attached to an indwelling urinary catheter. The port tube has a one-way valve located adjacent the second end. The second end is formed to fit sealably with a shaped nozzle.

(2) In a variant of the invention, a collection tube is provided. The collection tube has a proximal end and a distal end and has a shaped nozzle at the proximal end. The shaped nozzle is adapted to fit sealably into the port tube at the second end adjacent the one-way valve. A protective cover is provided. The cover is attached to the collection tube adjacent the proximal end, has a hollow interior and extends a first predetermined distance past an outer end of the shaped nozzle. A specimen container is provided. The container has a hollow body, a front end and a back end. The front end has an aperture. The aperture is sized and shaped to attach to the distal end of the collection tube. The aperture is sealable after removal of the distal end of the collection tube there from. A piston is provided. The piston fits closely within the hollow body and is attached to an actuating rod. When the port tube is connected to the collection tube, the collection tube is connected to the specimen container and the actuating rod is moved away from the front end of the container, urine will flow into the specimen container in a sterile condition.

(3) In another variant, the collection tube further includes a flexible portion between the proximal end and the distal end.

(4) In still another variant, the front end of the specimen container includes a rotating lid, the lid sealably closing the aperture.

(5) In yet another variant, a latching mechanism is provided. The latching mechanism controls rotation of the lid.

(6) In a further variant, the latching mechanism further includes a rotating portion. The rotating portion is affixed to a leading edge of the rotating lid and has a projecting ledge located parallel to the leading edge. A fixed portion is provided. The fixed portion is attached to the front end of the specimen container and has a receiving slot sized, shaped and located to mate frictionally with the projecting ledge. When the rotating lid is positioned to seal the aperture, the projecting ledge will be secured within the receiving slot.

(7) In still a further variant, the latching mechanism further includes a retracting tab attached to the rotating portion, the retracting tab assisting in opening the aperture.

(8) In yet a further variant, the piston further includes a seal. The seal has a front side and a back side and is sized and shaped to fit closely within the hollow body. The seal is located adjacent the front end of the specimen container. The seal has a central receiving port located at its center portion. A first end of the actuating rod is sized and shaped to removably engage the central receiving port. When the actuating rod has withdrawn the piston toward the back end of the specimen container, the actuating rod is removed from the receiving port, the aperture is sealed and the specimen container will contain a sterile urine sample.

(9) In another variant of the invention, the piston further includes a first seal. The first seal has a front side and a back side and is sized and shaped to fit closely within the hollow body. The first seal is located adjacent the front end of the specimen container. A second seal is provided. The second seal is sized and shaped to fit closely within the hollow body and has a central receiving port located at a center portion of the second seal. The second seal is spaced from the back side of the first seal and attached thereto at an outer surface of the receiving port. A first end of the actuating rod is sized and shaped to removably engage the central receiving port. When the actuating rod has withdrawn the piston toward the back end of the specimen container, the actuating rod is removed from the receiving port, the aperture is sealed and the specimen container will contain a sterile urine sample.

(10) In still another variant, the actuating rod has a male thread at the first end and the central receiving port has a mating female thread.

(11) In yet another variant, the distal end of the collection tube has an external thread and the aperture located at the front end of the specimen container has a mating internal thread.

(12) In a further variant, the collection tube further includes at least one lever to assist in attaching the collection tube to the aperture of the specimen container.

(13) In still a further variant, the one-way valve further includes a membrane formed of pliable material, the membrane has a central opening, and the opening is urged closed by an elastic nature of the membrane.

(14) In yet a further variant, the port tube is formed of resilient material, is rotatably attached at an opening in a side wall of the tubing of the urinary drainage system and further includes first and second sealing gaskets located adjacent the first end. The first sealing gasket is located upon an interior wall of the tubing and the second sealing gasket is located upon an exterior wall of the tubing.

(15) In another variant of the invention, the port tube further includes a base portion. The base portion has a hollow core with an attachment end and a first fitting end. The base portion is attached at the attachment end at an opening in a side wall of the tubing of the urinary drainage system. Inner and outer sealing gaskets are located adjacent the attachment end. The inner sealing gasket is located upon an interior wall of the tubing. The outer sealing gasket is located upon an exterior wall of the tubing. A tube portion is provided. The tube portion has a hollow interior, a second fitting end and a valve end. The second fitting end of the tube portion is rotatably attached to the first fitting end of the base portion. The tube portion has a one-way valve located adjacent the valve end.

(16) A closed specimen collection system for blood samples may be constructed from the following components. A collection tube is provided. The collection tube has a proximal end and a distal end and has a shaped nozzle at the proximal end. The shaped nozzle is adapted to fit sealably into a port connected to a centrally inserted venal catheter. A protective cover is provided. The cover is attached to the collection tube adjacent the proximal end, has a hollow interior and extends outwardly from a base of the shaped nozzle for a first predetermined distance. The cover has an internal, female thread. The female thread mates to a male thread on the port. A specimen container is provided. The container has a hollow body, a front end and a back end. The front end has an aperture. The aperture is sized and shaped to attach to the distal end of the collection tube. The aperture is sealable after removal of the distal end of the collection tube. A piston is provided. The piston fits closely within the hollow body and is attached to an actuating rod. When the port is connected to the collection tube, the collection tube is connected to the specimen container and the actuating rod is moved away from the front end of the container, blood will flow into the specimen container in a sterile condition.

(17) In a variant of the invention, the protective cover further includes at least one lever to assist in attaching the cover to the port.

(18) In another variant, the front end of the specimen container further includes a sample opening. The opening is sealed with a rubber membrane adapted to accommodate needle penetration.

(19) In yet another variant, the front end of the specimen container includes a rotating lid. The lid closes and seals the aperture.

(20) In a further variant, the lid for the specimen container further includes a latching mechanism. The latching mechanism controls rotation of the lid.

(21) In still a further variant, the latching mechanism further includes a rotating portion. The rotating portion is affixed to a leading edge of the rotating lid and has a projecting ledge located parallel to the leading edge. A fixed portion is provided. The fixed portion is affixed to the front end of the specimen container. The fixed portion has a receiving slot sized, shaped and located to mate frictionally with the projecting ledge. When the rotating lid is positioned to seal the aperture, the projecting ledge will be secured within the receiving slot.

(22) In yet a further variant, the latching mechanism further includes a retracting tab attached to the rotating portion, the retracting tab assists in opening the aperture.

(23) In another variant of the invention, the piston further includes a seal. The seal has a front side and a back side and is sized and shaped to fit closely within the hollow body. The seal is located adjacent the front end of the specimen container. The seal, has a central receiving port located at a center portion of the seal. A first end of the actuating rod is sized and shaped to removably engage the central receiving port. When the actuating rod has withdrawn the piston toward the back end of the specimen container, the actuating rod is removed from the receiving port, the aperture is sealed and the specimen container will contain a sterile blood sample.

(24) In still another variant, the piston further includes a first seal. The first seal has a front side and a back side and is sized and shaped to fit closely within the hollow body. The first seal is located adjacent the front end of the specimen container. A second seal is provided. The second seal is sized and shaped to fit closely within the hollow body and has a central receiving port penetrating a center portion of the second seal. The second seal is spaced from the back side of the first seal and attached to it at an outer surface of the receiving port. A first end of the actuating rod is sized and shaped to removably engage the central receiving port. When the actuating rod has withdrawn the piston toward the back end of the specimen container, the actuating rod is removed from the receiving port, the aperture is sealed and the specimen container will contain a sterile blood sample.

(25) In yet another variant, the actuating rod has a male thread at the first end and the central receiving port has a mating female thread.

(26) In a further variant, the distal end of the collection tube has an external thread and the aperture located at the front end of the specimen container has a mating internal thread.

(27) In a final variant of the invention the specimen container further includes a sterile culture medium.

An appreciation of the other aims and objectives of the present invention and an understanding of it may be achieved by referring to the accompanying drawings and the detailed description of a preferred embodiment.

DESCRIPTION OF THE DRAWINGS

FIG. 4 is a cross-sectional view of the FIG. 1 embodiment and a perspective view of a specimen container, with attached collection tube and shaped nozzle and protective cover;

FIG. 5 is a partial perspective view of an alternative specimen container in which the piston for urine withdrawal has two seals;

FIG. 5A is a partial perspective view of an alternative specimen container in which the piston is attached to the actuating rod with a round connector on a single seal;

FIG. 5B is a partial perspective view of an alternative specimen container in which the piston for urine withdrawal has two seals and the piston is attached to the actuating rod with a threaded connector;

DETAILED DESCRIPTION OF THE PREFERRED EMBODIMENT (1) FIGS. 1-8 illustrate a closed specimen collection system for urine 10 providing the desired features that may be constructed from the following components. A port tube 14 is provided. The port tube 14 has a first end 18, a second end 22 and is rotatably attached at the first end 18 to tubing 20 of a urinary drainage system 26 attached to an indwelling urinary catheter 30. The port tube 14 has a one-way valve 34 located adjacent the second end 22. The second end 22 is formed to fit sealably with a shaped nozzle 38.

Figure 1:
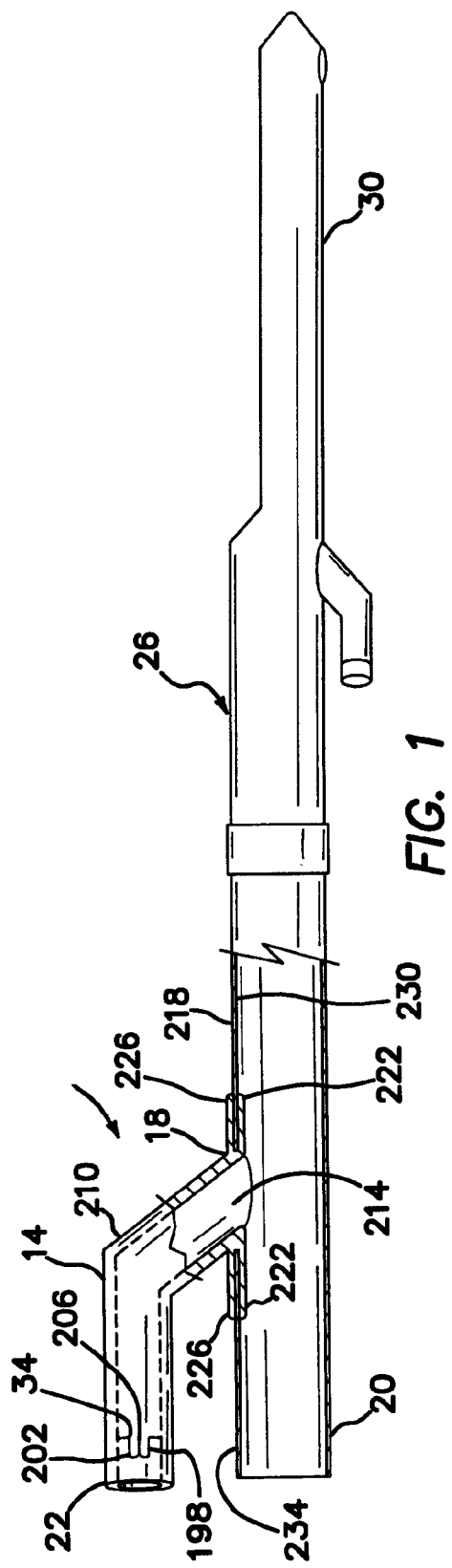
FIG. 1 is a side elevational view of the preferred embodiment of the invention attached to an indwelling catheter and urinary drainage system.

(2) In a variant of the invention, as illustrated in FIG. 4, a collection tube 42 is provided. The collection tube 42 has a proximal end 46 and a distal end 50 and has a shaped nozzle 38 at the proximal end 46. The shaped nozzle 38 is adapted to fit sealably into the port tube 14 at the second end 22 adjacent the one-way valve 34. A protective cover 54 is provided. The cover 54 is attached to the collection tube 42 adjacent the proximal end 46, has a hollow interior 58 and extends a first predetermined distance 62 past an outer end 66 of the shaped nozzle 38.

A specimen container 70 is provided. The container 70 has a hollow body 74, a front end 78 and a back end 82. The front end 78 has an aperture 86. The aperture 86 is sized and shaped to attach to the distal end 50 of the collection tube 42. The aperture 86 is sealable after removal of the distal end 50 of the collection tube 42 there from. A piston 90 is provided. The piston 90 fits closely within the hollow body 74 and is attached to an actuating rod 94. When the port tube 14 is connected to the collection tube 42, the collection tube 42 is connected to the specimen container 70 and the actuating rod 94 is moved away from the front end 78 of the container 70, urine (not shown) will flow into the specimen container 70 in a sterile condition.

(3) In another variant, the collection tube 42 further includes a flexible portion 80 between the proximal end 46 and the distal end 50.

Figure 7:
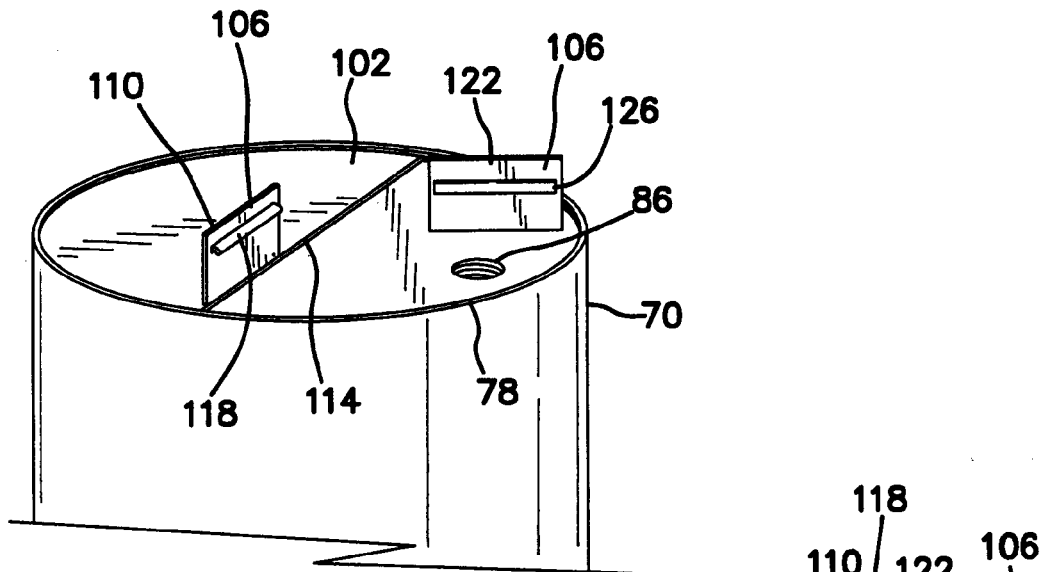
FIG. 7 is a partial perspective view of the specimen container illustrating a latching mechanism.

(4) In still another variant, as illustrated in FIGS. 4 and 7, the front end 78 of the specimen container 70 includes a rotating lid 102, the lid 102 sealably closing the aperture 86.

Figure 8:
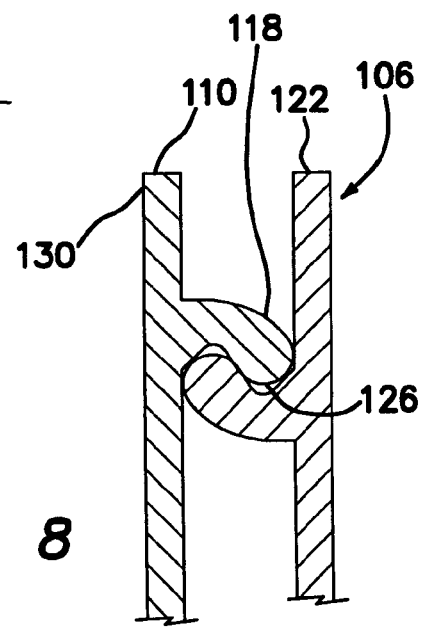
FIG. 8 is a cross-sectional side elevational view of a detail of the latching mechanism.

(5) In yet another variant, as illustrated in FIGS. 7 and 8, a latching mechanism 106 is provided. The latching mechanism 106 controls rotation of the lid 102.

(6) In a further variant, the latching mechanism 106 further includes a rotating portion 110. The rotating portion 110 is affixed to a leading edge 114 of the rotating lid 102 and has a projecting ledge 118 located parallel to the leading edge 114. A fixed portion 122 is provided. The fixed portion 122 is attached to the front end 78 of the specimen container 70 and has a receiving slot 126 sized, shaped and located to mate frictionally with the projecting ledge 118. When the rotating lid 102 is positioned to seal the aperture 86, the projecting ledge 118 will be secured within the receiving slot 126.

(7) In still a further variant, the latching mechanism 106 further includes a retracting tab 130 attached to the rotating portion 110, the retracting tab 130 assisting in opening the aperture 86.

(8) In yet a further variant, as illustrated in FIGS. 4 and 5A, the piston 90 further includes a seal 134. The seal 134 has a front side 138 and a back side 142 and is sized and shaped to fit closely within the hollow body 74. The seal 134 is located adjacent the front end 78 of the specimen container 70. The seal 134 has a central receiving port 146 located at its center portion 150. A first end 154 of the actuating rod 94 is sized and shaped to removably engage the central receiving port 146. When the actuating rod 94 has withdrawn the piston 90 toward the back end 82 of the specimen container 70, the actuating rod 94 is removed from the receiving port 146, the aperture 86 is sealed and the specimen container 70 will contain a sterile urine sample.

(9) In another variant of the invention, as illustrated in FIGS. 5 and 5B, the piston 90 further includes a first seal 158. The first seal 158 has a front side 162 and a back side 166 and is sized and shaped to fit closely within the hollow body 74. The first seal 158 is located adjacent the front end 78 of the specimen container 70. A second seal 170 is provided. The second seal 170 is sized and shaped to fit closely within the hollow body 74 and has a central receiving port 146 located at a center portion 150 of the second seal 170. The second seal 170 is spaced from the back side 166 of the first seal 158 and attached thereto at an outer surface 174 of the receiving port 146. A first end 154 of the actuating rod 94 is sized and shaped to removably engage the central receiving port 146. When the actuating rod 94 has withdrawn the piston 90 toward the back end 82 of the specimen container 70, the actuating rod 94 is removed from the receiving port 146, the aperture 86 is sealed and the specimen container 70 will contain a sterile urine sample 98.

(10) In still another variant, as illustrated in FIG. 5B, the actuating rod 94 has a male thread 178 at the first end 154 and the central receiving port 146 has a mating female thread 182.

Figure 6:
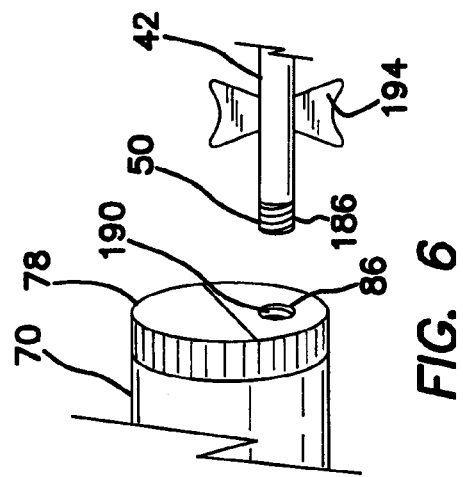
FIG. 6 is a partial perspective view of a threaded attachment to the collection tube to the specimen container.
Figure 2:
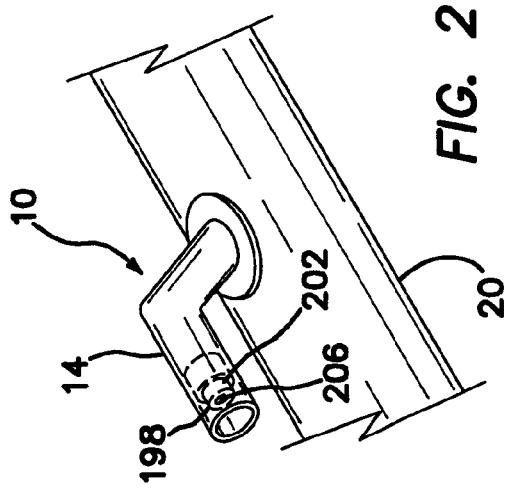
FIG. 2 is a perspective view of the FIG. 1 embodiment illustrating an internal one-way valve.

(11) In yet another variant, as illustrated in FIG. 6, the distal end 50 of the collection tube 42 has an external thread 186 and the aperture 86 located at the front end 78 of the specimen container 70 has a mating internal thread 190.

(12) In a further variant, the collection tube 42 further includes at least one lever 194 to assist in attaching the collection tube 42 to the aperture 86 of the specimen container 70.

(13) In still a further variant, as illustrated in FIGS. 1-4, the one-way valve 34 further includes a membrane 198 formed of pliable material 202, the membrane 198 has a central opening 206, and the opening 206 is urged closed by an elastic nature of the membrane 198.

(14) In yet a further variant, as illustrated in FIG. 1, the port tube 14 is formed of resilient material 210, is rotatably attached at an opening 214 in a side wall 218 of the tubing 20 of the urinary drainage system 26 and further includes first 222 and second 226 sealing gaskets located adjacent the first end 18. The first sealing gasket 222 is located upon an interior wall 230 of the tubing 20 and the second sealing gasket 226 is located upon an exterior wall 234 of the tubing 20.

Figure 3:
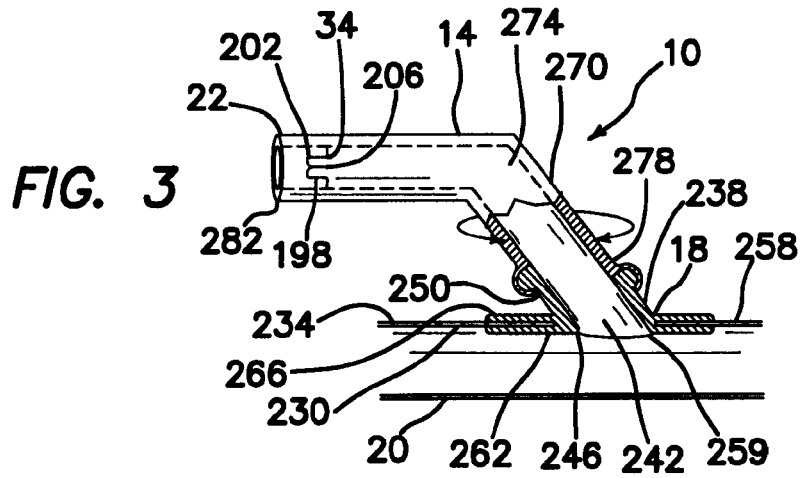
FIG. 3 is a side elevational view of a second embodiment providing an internal swivel feature.

(15) In another variant of the invention, as illustrated in FIG. 3, the port tube 14 further includes a base portion 238. The base portion 238 has a hollow core 242 with an attachment end 246 and a first fitting end 250. The base portion 238 is attached at the attachment end 246 at an opening 254 in a side wall 258 of the tubing 20 of the urinary drainage system 26. Inner 262 and outer 266 sealing gaskets are located adjacent the attachment end 246. The inner sealing gasket 262 is located upon an interior wall 230 of the tubing 20. The outer sealing gasket 266 is located upon an exterior wall 234 of the tubing 20. A tube portion 270 is provided. The tube portion 270 has a hollow interior 274, a second fitting end 278 and a valve end 282. The second fitting end 278 of the tube portion 270 is rotatably attached to the first fitting end 250 of the base portion 238. The tube portion 270 has a one-way valve 34 located adjacent the valve end 282.

Figure 9:
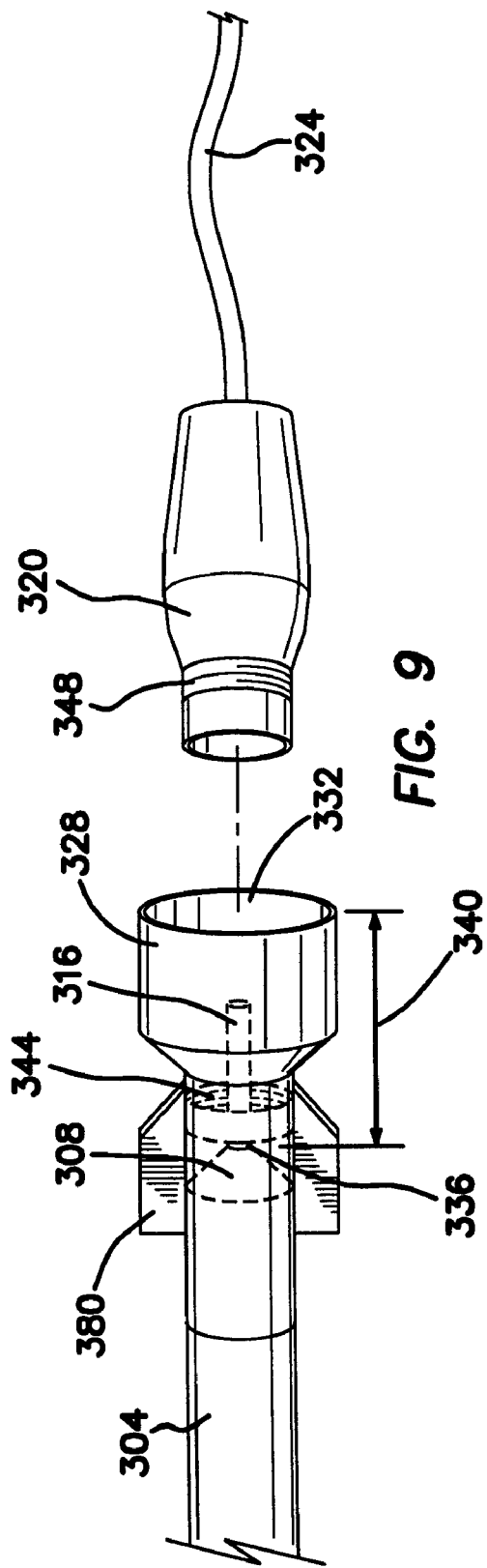
FIG. 9 is a perspective view of the collection tube of a closed specimen collection system for blood and a receiving port for a centrally inserted venal catheter.
Figure 12:
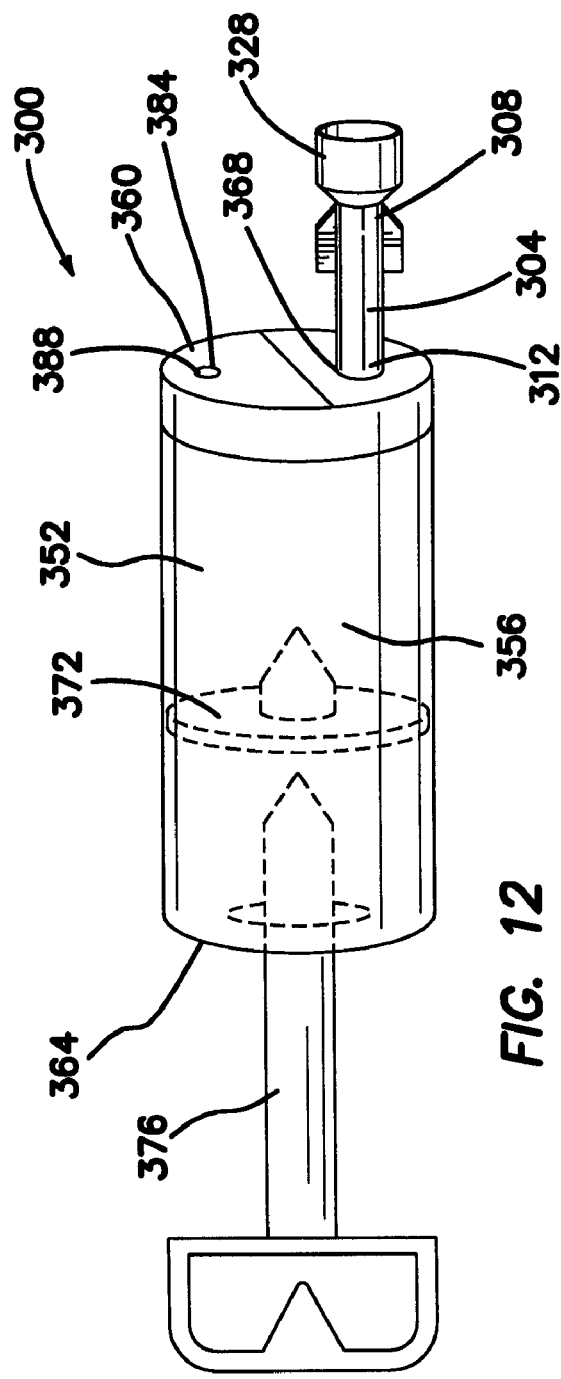
FIG. 12 is a perspective view of the closed specimen collection system for blood.

(16) A closed specimen collection system for blood samples 300, as illustrated in FIGS. 9 and 12, may be constructed from the following components. A collection tube 304 is provided. The collection tube 304 has a proximal end 308 and a distal end 312 and has a shaped nozzle 316 at the proximal end 308. The shaped nozzle 316 is adapted to fit sealably into a port 320 connected to a centrally inserted venal catheter 324. A protective cover 328 is provided. The cover 328 is attached to the collection tube 304 adjacent the proximal end 308, has a hollow interior 332 and extends outwardly from a base 336 of the shaped nozzle 316 for a first predetermined distance 340. The cover 328 has an internal, female thread 344. The female thread 344 mates to a male thread 348 on the port 320. A specimen container 352 is provided. The container 352 has a hollow body 356, a front end 360 and a back end 364. The front end 360 has an aperture 368. The aperture 368 is sized and shaped to attach to the distal end 312 of the collection tube 304. The aperture 368 is sealable after removal of the distal end 312 of the collection tube 304. A piston 372 is provided. The piston 372 fits closely within the hollow body 356 and is attached to an actuating rod 376. When the port 320 is connected to the collection tube 304, the collection tube 304 is connected to the specimen container 352 and the actuating rod 376 is moved away from the front end 360 of the container 352, blood will flow into the specimen container 352 in a sterile condition.

(17) In a variant of the invention, the protective cover 328 further includes at least one lever 380 to assist in attaching the cover 328 to the port 320.

Figure 10:
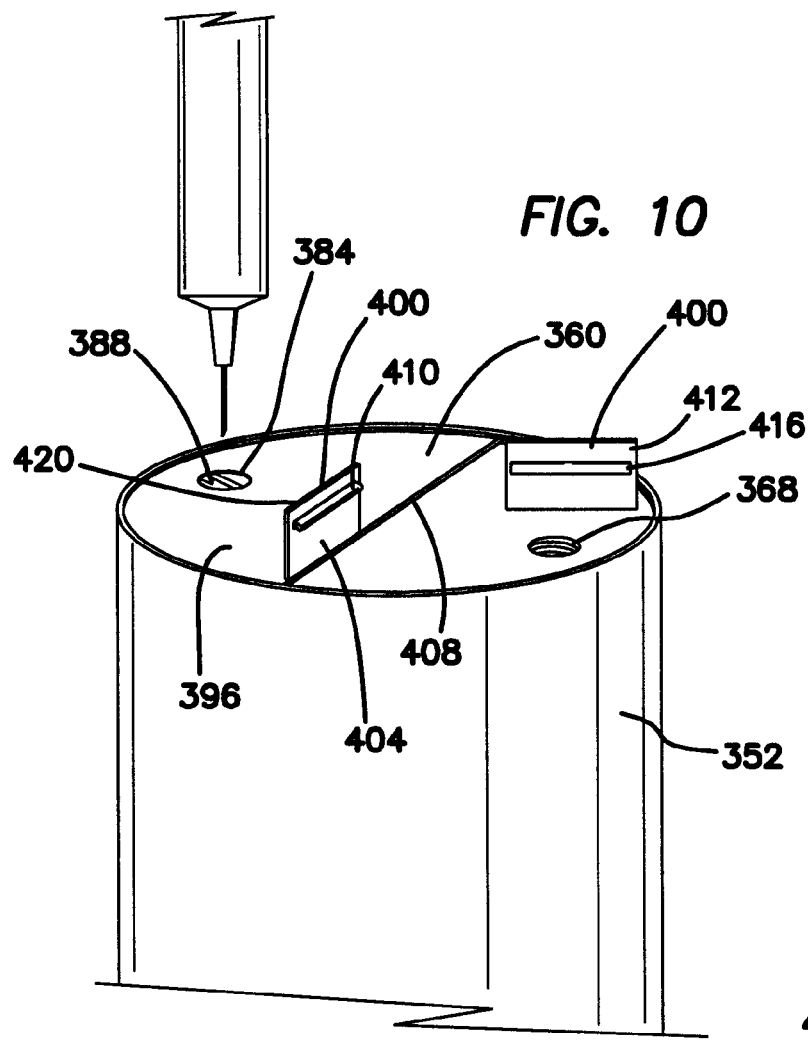
FIG. 10 is an enlarged perspective view of a specimen container illustrating a latching mechanism, sample port and aperture for attachment of the collection tube.

(18) In another variant, as illustrated in FIGS. 10 and 12, the front end 360 of the specimen container 352 further includes a sample opening 384. The opening 384 is sealed with a rubber membrane 388 adapted to accommodate needle penetration.

(19) In yet another variant, the front end 360 of the specimen container 352 includes a rotating lid 396. The lid 396 closes and seals the aperture 368.

(20) In a further variant, the lid 396 for the specimen container 352 further includes a latching mechanism 400. The latching mechanism 400 controls rotation of the lid 396.

Figure 11:
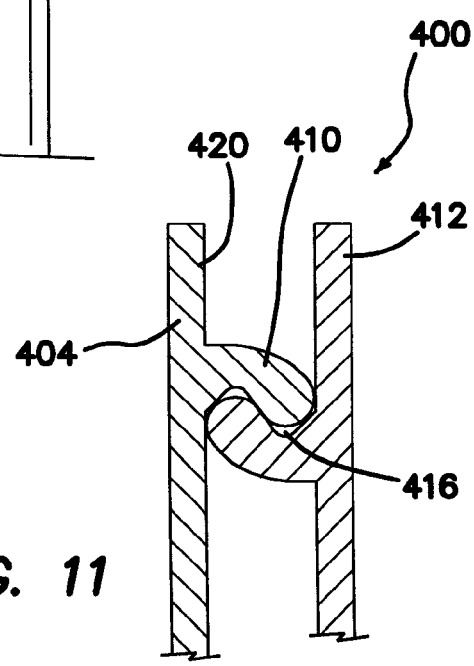
FIG. 11 is a cross-sectional detail view of the latching mechanism.

(21) In still a further variant, as illustrated in FIGS. 10 and 11, the latching mechanism 400 further includes a rotating portion 404. The rotating portion 404 is affixed to a leading edge 408 of the rotating lid 396 and has a projecting ledge 410 located parallel to the leading edge 408. A fixed portion 412 is provided. The fixed portion 412 is affixed to the front end 360 of the specimen container 352. The fixed portion 412 has a receiving slot 416 sized, shaped and located to mate frictionally with the projecting ledge 408. When the rotating lid 396 is positioned to seal the aperture 368, the projecting ledge 408 will be secured within the receiving slot 416.

(22) In yet a further variant, the latching mechanism 400 further includes a retracting tab 420 attached to the rotating portion 404, the retracting tab 420 assists in opening the aperture 368.

Figure 13:
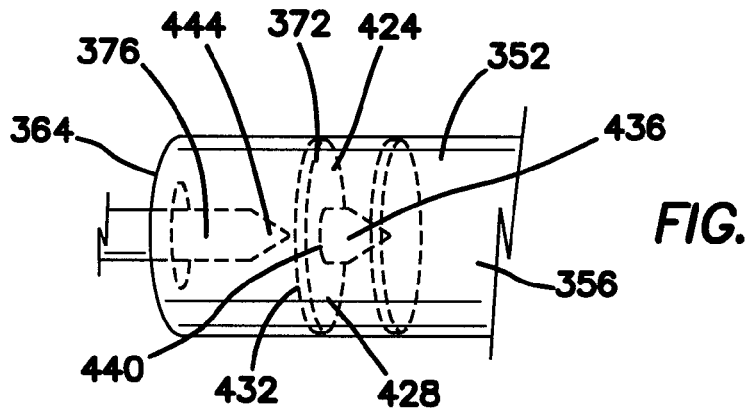
FIG. 13 is a perspective view of the back end of the specimen container of the FIG. 12 embodiment illustrating details of a first embodiment of the piston of the specimen container.

(23) In another variant of the invention, as illustrated in FIG. 13, the piston 372 further includes a seal 424. The seal 424 has a front side 428 and a back side 432 and is sized and shaped to fit closely within the hollow body 356. The seal 424 is located adjacent the front end 360 of the specimen container 352. The seal 424, has a central receiving port 436 located at a center portion 440 of the seal 424. A first end 444 of the actuating rod 376 is sized and shaped to removably engage the central receiving port 436. When the actuating rod 376 has withdrawn the piston 372 toward the back end 364 of the specimen container 352, the actuating rod 376 is removed from the receiving port 436, the aperture 368 is sealed and the specimen container 352 will contain a sterile blood sample.

Figure 14:
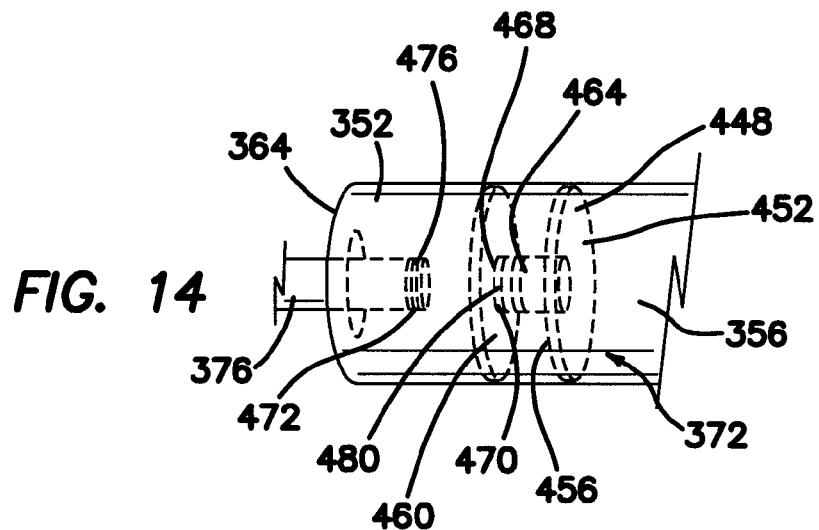
FIG. 14 is a perspective view of the back end of the specimen container of the FIG. 12 embodiment illustrating details of a second embodiment of the piston of the specimen container having two seals and a screw fitting for attachment of an activating rod to the piston.
Figure 15:
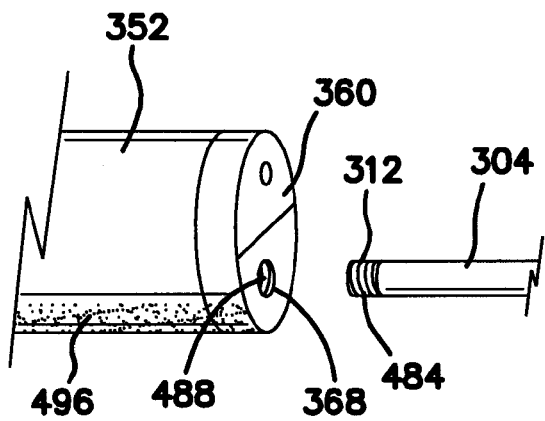
FIG. 15 is a perspective view of the front end of the specimen container illustrating the sample port and a screw fitting for attachment of the collection tube to the aperture.

(24) In still another variant, as illustrated in FIG. 14, the piston 372 further includes a first seal 448. The first seal 448 has a front side 452 and a back side 456 and is sized and shaped to fit closely within the hollow body 356. The first seal 448 is located adjacent the front end 360 of the specimen container 352. A second seal 460 is provided. The second seal 460 is sized and shaped to fit closely within the hollow body 356 and has a central receiving port 464 penetrating a center portion 468 of the second seal 460. The second seal 460 is spaced from the back side 456 of the first seal 448 and attached to it at an outer surface 470 of the receiving port 464. A first end 472 of the actuating rod 376 is sized and shaped to removably engage the central receiving port 464. When the actuating rod 376 has withdrawn the piston 372 toward the back end 364 of the specimen container 352, the actuating rod 376 is removed from the receiving port 464, the aperture 368 is sealed and the specimen container 352 will contain a sterile blood sample.

(25) In yet another variant, the actuating rod 376 has a male thread 476 at the first end 472 and the central receiving port 464 has a mating female thread 480.

(26) In a further variant, the distal end 312 of the collection tube 304 has an external thread 484 and the aperture 368 located at the front end 360 of the specimen container 352 has a mating internal thread 488.

(27) In a final variant of the invention the specimen container 352 further includes a sterile culture medium 496.

The closed specimen collection systems 10 and 300 have been described with reference to particular embodiments. Other modifications and enhancements can be made without departing from the spirit and scope of the claims that follow.

The invention claimed is:
1. A closed specimen collection system, comprising:
 a collection tube, said collection tube having a proximal end and a distal end and having a blunt, shaped nozzle at said proximal end;
 said shaped nozzle being adapted to fit sealably into a port connected axially to a distal end of a centrally inserted venal catheter;
 a protective cover, said cover being attached to said collection tube adjacent said proximal end, said cover having a hollow interior and extending outwardly from a base of said shaped nozzle a first predetermined distance;
 said cover having an internal, female thread, said female thread mating to a male thread on said port;
 a specimen container, said container having a hollow body, a front a back end and a longitudinal axis;
 said front end having an aperture, said aperture being sized and shaped to attach to said distal end of said collection tube, an integral axially rotating lid, said lid rotating about said longitudinal axis and sealing said aperture after removal of said distal end of said collection tube;
 a latching mechanism, said latching mechanism controlling rotation of said lid;
 a piston, said piston fitting closely within said hollow body and being attached to an actuating rod; and
 whereby, when said port is connected to said collection tube, said collection tube is connected to said specimen container and said actuating rod is moved away from said front end of said container, blood will flow into said specimen container in a sterile condition.

2. The closed specimen collection system, as described in claim 1, wherein said protective cover further comprises at least one lever to assist in attaching said cover to said port.

3. The closed specimen collection system, as described in claim 1, wherein said front end of said specimen container further comprises a sample opening, said opening being sealed with a rubber membrane, said membrane adapted to accommodate needle penetration.

4. The closed specimen collection system, as described in claim 1, wherein said latching mechanism further comprises:
 a rotating portion, said rotating portion affixed to a leading edge of said rotating lid, said rotating lid rotating to seal said aperture, and having a projecting ledge disposed parallel to said leading edge;
 a fixed portion, said fixed portion affixed to said front end of said specimen container, having a receiving slot sized, shaped and disposed to mate frictionally with said projecting ledge; and
 whereby, when said rotating lid is positioned to seal said aperture, said projecting ledge will be secured within said receiving slot.

5. The closed specimen collection system, as described in claim 4, wherein said latching mechanism further comprises a retracting tab attached to said rotating portion, said retracting tab assisting in opening said aperture.

6. The closed specimen collection system, as described in claim 1, wherein said piston further comprises:

a seal, said seal having a front side and a back side and being sized and shaped to fit closely within said hollow body and disposed adjacent said front end of said specimen container;

said seal, having a central receiving port disposed at a center portion thereof;

a first end of said actuating rod being sized and shaped to removably engage said central receiving port; and whereby, when said actuating rod has withdrawn said piston toward said back end of said specimen container, said actuating rod is removed from said receiving port and when said aperture is sealed said specimen container will contain a sterile blood sample.

7. The closed specimen collection system, as described in claim 1, wherein said piston further comprises:

a first seal, said first seal having a front side and a back side and being sized and shaped to fit closely within said hollow body and disposed adjacent said front end of said specimen container;

a second seal, said second seal being sized and shaped to fit closely within said hollow body and having a central receiving port penetrating a center portion of said second seal;

said second seal being spaced from said back side of said first seal and attached thereto at an outer surface of said receiving port;

a first end of said actuating rod being sized and shaped to removably engage said central receiving port; and whereby, when said actuating rod has withdrawn said piston toward said back end of said specimen container, said actuating rod is removed from said receiving port, said aperture is sealed and said specimen container will contain a sterile blood sample.

8. The closed specimen collection system, as described in claim 7, wherein said actuating rod has a male thread at said first end and said central receiving port has a mating female thread.

9. The closed specimen collection system, as described in claim 1, wherein said distal end of said collection tube has an external thread and said aperture disposed at said front end of said specimen container has a mating internal thread.

10. The closed specimen collection system, as described in claim 1, wherein said specimen container further comprises a sterile culture medium.

* * * * *